(12) United States Patent  
Ballesteros et al.

(10) Patent No.: US 9,168,209 B2
(45) Date of Patent: *Oct. 27, 2015

(54) PIGMENTED SKIN-CARE COMPOSITIONS

(71) Applicant: Johnson & Johnson Consumer Companies, Inc., Skillman, NJ (US)

(72) Inventors: Ann Theodore Ballesteros, New Brunswick, NJ (US); Stephen William Pitt, Huntingdon Valley, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/799,066

(22) Filed: Mar. 13, 2013

(65) Prior Publication Data

US 2014/0271738 A1   Sep. 18, 2014

(51) Int. Cl.
- *A61K 8/02* (2006.01)
- *A61Q 1/02* (2006.01)
- *A61Q 19/00* (2006.01)

(52) U.S. Cl.
CPC ............... *A61K 8/0245* (2013.01); *A61Q 1/02* (2013.01); *A61Q 19/00* (2013.01); *A61K 2800/412* (2013.01); *A61K 2800/436* (2013.01)

(58) Field of Classification Search
CPC ....................................................... A61Q 1/02
See application file for complete search history.

(56) References Cited

U.S. PATENT DOCUMENTS

| | | |
|---|---|---|
| 3,692,768 A | 9/1972 | Takata |
| 3,978,207 A | 8/1976 | Fotiu |
| 4,456,486 A | 6/1984 | Bernhard |
| 4,457,784 A | 7/1984 | Bernhard |
| 4,494,993 A | 1/1985 | Bernhard |
| 4,552,593 A | 11/1985 | Ostertag |
| 4,565,581 A | 1/1986 | Bernhard |
| 4,623,396 A | 11/1986 | Kimura |
| 4,648,908 A | 3/1987 | Takasuka |
| 4,710,375 A | 12/1987 | Takasuka |
| 4,828,826 A | 5/1989 | Franz |
| 4,952,245 A | 8/1990 | Iwano |
| 5,116,664 A | 5/1992 | Kimura |
| 5,156,678 A | 10/1992 | Glausch |
| 5,169,442 A | 12/1992 | Noguchi |
| 5,302,199 A | 4/1994 | Prengel |
| 5,326,392 A | 7/1994 | Miller |
| 5,364,467 A | 11/1994 | Schmid |
| 5,496,543 A | 3/1996 | Lagrange |
| 5,607,504 A | 3/1997 | Schmid |
| 5,618,342 A | 4/1997 | Herget |
| 5,624,486 A | 4/1997 | Schmid |
| 5,624,487 A | 4/1997 | Schmidt |
| 5,624,731 A | 4/1997 | Desjardins |
| 5,662,738 A | 9/1997 | Schmid |
| 5,690,916 A | 11/1997 | Kimura |
| 5,733,658 A | 3/1998 | Schmid |
| 5,741,355 A | 4/1998 | Yamamoto |
| 5,753,026 A | 5/1998 | Kuntz |
| 5,776,497 A | 7/1998 | Lagrange |
| 5,807,497 A | 9/1998 | Gailberger |
| 5,851,277 A | 12/1998 | Muller Rees |
| 5,958,125 A | 9/1999 | Schmid |
| 5,972,098 A | 10/1999 | Andes |
| 6,001,373 A | 12/1999 | Igo Kemenes |
| 6,113,683 A | 9/2000 | Herren |
| 6,117,435 A | 9/2000 | Painter |
| 6,132,504 A | 10/2000 | Kuntz |
| 6,132,873 A | 10/2000 | Dietz |
| 6,156,115 A | 12/2000 | Pfaff |
| 6,187,298 B1 | 2/2001 | Kurz |
| 6,190,445 B1 | 2/2001 | Noguchi |
| 6,190,648 B1 | 2/2001 | Kouzu |
| 6,238,471 B1 | 5/2001 | Vogt |
| 6,238,472 B1 | 5/2001 | Andes |
| 6,267,810 B1 | 7/2001 | Pfaff |
| 6,280,520 B1 | 8/2001 | Andes |
| 6,306,409 B1 | 10/2001 | Ogawa |
| 6,428,773 B1 | 8/2002 | Oko |
| 6,451,294 B1 | 9/2002 | Simon |
| 6,475,500 B2 | 11/2002 | Vatter |
| 6,485,556 B1 | 11/2002 | DeLuca, Jr. |
| 6,500,251 B1 | 12/2002 | Andes |
| 6,508,876 B1 | 1/2003 | Bernhardt |
| 6,511,672 B2 | 1/2003 | Tan |
| 6,517,628 B1 | 2/2003 | Pfaff |
| 6,524,598 B2 | 2/2003 | Sunkel |
| 6,531,221 B1 | 3/2003 | Schuhmacher |
| 6,545,809 B1 | 4/2003 | Phillips |
| 6,579,355 B1 | 6/2003 | Schmidt |
| 6,596,070 B1 | 7/2003 | Schmidt |
| 6,599,355 B1 | 7/2003 | Schmidt |
| 6,630,018 B2 | 10/2003 | Bauer |
| 6,632,275 B1 | 10/2003 | Schoen |
| 6,641,823 B2 | 11/2003 | Piot |

(Continued)

FOREIGN PATENT DOCUMENTS

| | | |
|---|---|---|
| EP | 959109 B1 | 2/1977 |
| EP | 95889 A3 | 9/1984 |

(Continued)

*Primary Examiner* — Ileana Popa
*Assistant Examiner* — Nicole Babson

(57) ABSTRACT

A pigmented skin care composition including a dermatologically acceptable carrier and at least a first and second interference pigment. The composition according to the invention is useful in improving the appearance of the skin and in particular in reducing the appearance of skin discontinuities.

12 Claims, No Drawings

(56) References Cited

U.S. PATENT DOCUMENTS

| | | |
|---|---|---|
| 6,641,874 B2 | 11/2003 | Kuntz |
| 6,648,957 B1 | 11/2003 | Andes |
| 6,656,259 B2 | 12/2003 | Pfaff |
| 6,663,852 B2 | 12/2003 | Simon |
| 6,689,205 B1 | 2/2004 | Brückner |
| 6,692,561 B1 | 2/2004 | Schoen |
| 6,696,049 B2 | 2/2004 | Vatter |
| 6,706,109 B2 | 3/2004 | DeLuca, Jr. |
| 6,719,837 B2 | 4/2004 | Bertaux |
| 6,719,838 B2 | 4/2004 | Heider |
| 6,743,285 B1 | 6/2004 | Anselmann |
| 6,744,559 B2 | 6/2004 | Phillips |
| 6,747,073 B1 | 6/2004 | Pfaff |
| 6,749,936 B2 | 6/2004 | Argoitia |
| 6,751,022 B2 | 6/2004 | Phillips |
| 6,773,499 B2 | 8/2004 | Schoen |
| 6,783,584 B2 | 8/2004 | Takahashi |
| 6,794,037 B2 | 9/2004 | Zimmermann |
| 6,800,125 B2 | 10/2004 | Zimmermann |
| 6,821,333 B2 | 11/2004 | Zimmermann |
| 6,831,785 B2 | 12/2004 | Phillips |
| 6,833,959 B2 | 12/2004 | Phillips |
| 6,837,925 B2 | 1/2005 | Kubo |
| 6,840,993 B2 | 1/2005 | Schmidt |
| 6,875,264 B2 | 4/2005 | Zimmermann |
| 6,884,289 B2 | 4/2005 | Schoen |
| 6,906,015 B1 | 6/2005 | Shiloach |
| 7,014,700 B2 | 3/2006 | DeLuca, Jr. |
| 7,045,007 B2 | 5/2006 | Bagala, Sr. |
| 7,060,126 B2 | 6/2006 | Andes |
| 7,077,897 B2 | 7/2006 | Brueckner |
| 7,169,223 B1 | 1/2007 | Pfaff |
| 7,202,199 B2 | 4/2007 | Shiloach |
| 7,226,503 B2 | 6/2007 | Anselmann |
| 7,241,503 B2 | 7/2007 | Noguchi |
| 7,255,736 B2 | 8/2007 | Pfaff |
| 7,264,670 B2 | 9/2007 | Rüger |
| 7,300,510 B2 | 11/2007 | Seeger |
| 7,303,622 B2 | 12/2007 | Loch |
| 7,318,861 B2 | 1/2008 | Bagala, Sr. |
| 7,326,671 B2 | 2/2008 | Shiloach |
| 7,344,590 B2 | 3/2008 | Schmidt |
| 7,365,109 B2 | 4/2008 | Rathschlag |
| 7,387,669 B2 | 6/2008 | Mronga |
| 7,396,401 B2 | 7/2008 | Jungnitz |
| 7,452,597 B2 | 11/2008 | Bujard |
| 7,455,726 B2 | 11/2008 | Schoenefeld |
| 7,479,323 B2 | 1/2009 | Rathschlag |
| 7,485,183 B2 | 2/2009 | Hochstein |
| 7,517,404 B2 | 4/2009 | Bujard |
| 7,531,184 B2 | 5/2009 | Horino |
| 7,578,879 B2 | 8/2009 | Huber |
| 7,579,079 B2 | 8/2009 | Huber |
| 7,604,862 B2 | 10/2009 | Ambrosius |
| 7,621,966 B2 | 11/2009 | Brun |
| 7,628,998 B2 | 12/2009 | Shah |
| 7,682,604 B2 | 3/2010 | Ogawa |
| 7,691,196 B2 | 4/2010 | Pfaff |
| 7,708,823 B2 | 5/2010 | Kniess |
| 7,745,003 B2 | 6/2010 | Hennemann |
| 7,767,214 B2 | 8/2010 | Simon |
| 7,772,214 B2 | 8/2010 | Vatter |
| 7,780,955 B2 | 8/2010 | Cassin |
| 7,794,740 B2 | 9/2010 | Cohen |
| 7,799,746 B2 | 9/2010 | Patel |
| 7,820,150 B2 | 10/2010 | Kohlhase |
| 7,828,890 B2 | 11/2010 | Henglein |
| 7,850,775 B2 | 12/2010 | Hollman |
| 7,875,112 B2 | 1/2011 | Huber |
| 7,959,727 B2 | 6/2011 | Bujard |
| 7,993,443 B2 | 8/2011 | Fuller |
| 7,993,444 B2 | 8/2011 | Fuller |
| 7,998,266 B2 | 8/2011 | Morimitsu |
| 8,007,583 B2 | 8/2011 | Fuller |
| 8,016,934 B2 | 9/2011 | Misaki |
| 8,067,090 B2 | 11/2011 | Domnick |
| 8,083,846 B2 | 12/2011 | Zimmermann |
| 8,088,212 B2 | 1/2012 | Bagala, Sr. |
| 8,088,214 B2 | 1/2012 | Fuller |
| 8,114,211 B2 | 2/2012 | Handrosch |
| 8,114,388 B2 | 2/2012 | Simon |
| 8,129,021 B2 | 3/2012 | Kaupp |
| 8,147,853 B2 | 4/2012 | Taylor |
| 8,158,566 B2 | 4/2012 | Wei |
| 2001/0001174 A1 | 5/2001 | Andes |
| 2002/0018790 A1 | 2/2002 | Vatter |
| 2002/0018791 A1 | 2/2002 | Vatter |
| 2002/0033117 A1 | 3/2002 | Inoue |
| 2002/0064509 A1 | 5/2002 | Grimm |
| 2002/0134282 A1 | 9/2002 | Ostertag |
| 2002/0169244 A1 | 11/2002 | Ostertag |
| 2003/0017124 A1 | 1/2003 | Agostini |
| 2003/0017280 A1 | 1/2003 | Poetsch |
| 2003/0064039 A1 | 4/2003 | Kolodziej |
| 2003/0075079 A1 | 4/2003 | Sommer |
| 2003/0091813 A1 | 5/2003 | Fuller |
| 2003/0118622 A1 | 6/2003 | Ramin |
| 2003/0157041 A1 | 8/2003 | Dreher |
| 2003/0157042 A1 | 8/2003 | Collin |
| 2003/0209169 A1 | 11/2003 | Andes |
| 2003/0211058 A1 | 11/2003 | Matts |
| 2004/0052743 A1 | 3/2004 | Schmidt |
| 2004/0057915 A1 | 3/2004 | Gers-Barlag |
| 2004/0076650 A1 | 4/2004 | Blin |
| 2004/0105827 A1 | 6/2004 | Grimm |
| 2004/0177788 A1 | 9/2004 | Rick |
| 2004/0191198 A1 | 9/2004 | Hochstein |
| 2004/0194663 A1 | 10/2004 | Li |
| 2004/0219116 A1 | 11/2004 | Reynders |
| 2004/0223991 A1 | 11/2004 | Wei |
| 2004/0223992 A1 | 11/2004 | Clapp |
| 2004/0223993 A1 | 11/2004 | Clapp |
| 2004/0234564 A1 | 11/2004 | Blin |
| 2004/0234565 A1 | 11/2004 | Stella |
| 2004/0241118 A1 | 12/2004 | Simon |
| 2004/0258640 A1 | 12/2004 | Simon |
| 2005/0001203 A1 | 1/2005 | Bertaux |
| 2005/0008595 A1 | 1/2005 | Duffournier |
| 2005/0061205 A1 | 3/2005 | Kobayashi |
| 2005/0112072 A1 | 5/2005 | Wang |
| 2005/0142084 A1 | 6/2005 | Ganguly |
| 2005/0143269 A1 | 6/2005 | Wei |
| 2005/0164896 A1 | 7/2005 | Dabkowski |
| 2005/0175562 A1 | 8/2005 | Hadasch |
| 2005/0176850 A1 | 8/2005 | Schmidt |
| 2005/0204958 A1 | 9/2005 | Kuebelbeck |
| 2005/0220735 A1 | 10/2005 | Tsaur |
| 2005/0220736 A1 | 10/2005 | Polonka |
| 2005/0252410 A1 | 11/2005 | Bujard |
| 2005/0268405 A1 | 12/2005 | Brun |
| 2005/0273947 A1 | 12/2005 | Brun |
| 2005/0276768 A1 | 12/2005 | Wei |
| 2005/0276779 A1 | 12/2005 | Blin |
| 2006/0005742 A1 | 1/2006 | Moeschl |
| 2006/0013838 A1 | 1/2006 | Peng |
| 2006/0027140 A1 | 2/2006 | Kniess |
| 2006/0032404 A1 | 2/2006 | Kniess |
| 2006/0034787 A1 | 2/2006 | Bujard |
| 2006/0047018 A1 | 3/2006 | Li |
| 2006/0051204 A1 | 3/2006 | Lyons |
| 2006/0051304 A1 | 3/2006 | Peng |
| 2006/0088483 A1 | 4/2006 | Thevenet |
| 2006/0144294 A1 | 7/2006 | Misaki |
| 2006/0147390 A1 | 7/2006 | Schreiber |
| 2006/0156949 A1 | 7/2006 | Pfaff |
| 2006/0159920 A1 | 7/2006 | Reynders |
| 2006/0225609 A1 | 10/2006 | Rueger |
| 2006/0241211 A1 | 10/2006 | Coughlin |
| 2006/0280705 A1 | 12/2006 | Bruechert |
| 2006/0280706 A1 | 12/2006 | Sebillotte-Arnaud |
| 2007/0028799 A1 | 2/2007 | Kniess |
| 2007/0048237 A1 | 3/2007 | Song |
| 2007/0065381 A1 | 3/2007 | Elsbrock |
| 2007/0077218 A1 | 4/2007 | Weinling |

(56) References Cited

U.S. PATENT DOCUMENTS

| | | |
|---|---|---|
| 2007/0134174 A1 | 6/2007 | Irwin |
| 2007/0134177 A1 | 6/2007 | Zimmermann |
| 2007/0141001 A1 | 6/2007 | Clapp |
| 2007/0141002 A1 | 6/2007 | Montezinos |
| 2007/0166534 A1 | 7/2007 | Entenmann |
| 2007/0225424 A1 | 9/2007 | Schulz |
| 2007/0248560 A1 | 10/2007 | Livoreil |
| 2007/0274938 A1 | 11/2007 | Alfano |
| 2007/0297996 A1 | 12/2007 | Tanner |
| 2008/0019933 A1 | 1/2008 | Thevenet |
| 2008/0038360 A1 | 2/2008 | Zukowski |
| 2008/0044366 A1 | 2/2008 | Dumousseaux |
| 2008/0081057 A1 | 4/2008 | Chevalier |
| 2008/0102269 A1 | 5/2008 | Herzing |
| 2008/0105272 A1 | 5/2008 | Thevenet |
| 2008/0127429 A1 | 6/2008 | Brun |
| 2008/0168924 A1 | 7/2008 | Melson |
| 2008/0181921 A1 | 7/2008 | DeLuca |
| 2008/0200560 A1 | 8/2008 | Kniess |
| 2008/0207772 A1 | 8/2008 | Kniess |
| 2008/0210133 A1 | 9/2008 | Roesler |
| 2008/0213322 A1 | 9/2008 | Birman |
| 2008/0226574 A1 | 9/2008 | Thevenet |
| 2008/0247977 A1 | 10/2008 | Le Gendre |
| 2008/0249209 A1 | 10/2008 | Trummer |
| 2008/0279796 A1 | 11/2008 | Handrosch |
| 2008/0279899 A1 | 11/2008 | Geffroy |
| 2008/0292567 A1 | 11/2008 | Schuster |
| 2008/0295737 A1 | 12/2008 | Henglein |
| 2008/0314284 A1 | 12/2008 | Li |
| 2008/0319089 A1 | 12/2008 | Muller |
| 2009/0011035 A1 | 1/2009 | Zukowski |
| 2009/0013906 A1 | 1/2009 | Fischer |
| 2009/0028808 A1 | 1/2009 | Cetti |
| 2009/0028809 A1 | 1/2009 | Cetti |
| 2009/0030113 A1 | 1/2009 | Glockner |
| 2009/0035241 A1 | 2/2009 | Cassin |
| 2009/0041695 A1 | 2/2009 | Dumousseaux |
| 2009/0053164 A1 | 2/2009 | Opper-Linnert |
| 2009/0056591 A1 | 3/2009 | Schmidt |
| 2009/0123403 A1 | 5/2009 | Barba |
| 2009/0185992 A1 | 7/2009 | Conan |
| 2009/0196841 A1 | 8/2009 | Song |
| 2009/0208436 A1 | 8/2009 | Hollman |
| 2009/0220557 A1 | 9/2009 | Pfaff |
| 2009/0246294 A1 | 10/2009 | Hochstein |
| 2009/0249979 A1 | 10/2009 | Kaupp |
| 2009/0252695 A1 | 10/2009 | Peng |
| 2009/0252772 A1 | 10/2009 | Henglein |
| 2009/0311209 A1 | 12/2009 | Bujard |
| 2010/0011992 A1 | 1/2010 | Bujard |
| 2010/0047291 A1 | 2/2010 | Hochstein |
| 2010/0047300 A1 | 2/2010 | Kaupp |
| 2010/0089291 A1 | 4/2010 | Kang |
| 2010/0095868 A1 | 4/2010 | Kaupp |
| 2010/0104610 A1 | 4/2010 | Dueva-Koganov |
| 2010/0116169 A1 | 5/2010 | Kaupp |
| 2010/0129412 A1 | 5/2010 | Kitamura |
| 2010/0136068 A1 | 6/2010 | Perier |
| 2010/0158830 A1 | 6/2010 | Wei |
| 2010/0178308 A1 | 7/2010 | Iwasa |
| 2010/0183535 A1 | 7/2010 | Goetz |
| 2010/0192802 A1 | 8/2010 | Bujard |
| 2010/0196296 A1 | 8/2010 | Geissler |
| 2010/0197805 A1 | 8/2010 | Cassin |
| 2010/0203093 A1 | 8/2010 | Bujard |
| 2010/0209464 A1 | 8/2010 | Maderazzo |
| 2010/0218703 A1 | 9/2010 | Bujard |
| 2010/0221205 A1 | 9/2010 | Blin |
| 2010/0297045 A1 | 11/2010 | Kaupp |
| 2010/0322883 A1 | 12/2010 | Gohier |
| 2010/0322981 A1 | 12/2010 | Bujard |
| 2011/0033400 A1 | 2/2011 | Ehlis |
| 2011/0064779 A1 | 3/2011 | Gruener |
| 2011/0070273 A1 | 3/2011 | Zheng |
| 2011/0112234 A1 | 5/2011 | Hall-Goulle |
| 2011/0113984 A1 | 5/2011 | Fuller, Jr. |
| 2011/0118384 A1 | 5/2011 | Bugnon |
| 2011/0212042 A1 | 9/2011 | Maitra |
| 2011/0223218 A1 | 9/2011 | Jones |
| 2011/0226161 A1 | 9/2011 | Schumacher |
| 2011/0236332 A1 | 9/2011 | Dop |
| 2011/0237683 A1 | 9/2011 | Schmid |
| 2011/0251293 A1 | 10/2011 | Trummer |
| 2011/0269845 A1 | 11/2011 | Bujard |
| 2011/0298207 A1 | 12/2011 | Despland |
| 2011/0306678 A1 | 12/2011 | Liu |
| 2012/0027862 A1 | 2/2012 | Schmidt |
| 2012/0039833 A1 | 2/2012 | Brennan |
| 2012/0091702 A1 | 4/2012 | Shimizu |

FOREIGN PATENT DOCUMENTS

| | | |
|---|---|---|
| EP | 246523 B1 | 1/1991 |
| EP | 307747 B1 | 5/1992 |
| EP | 381047 B1 | 8/1994 |
| EP | 555325 B1 | 11/1994 |
| EP | 562329 B1 | 7/1995 |
| EP | 580022 B1 | 1/1996 |
| EP | 632110 B1 | 9/1996 |
| EP | 655486 B1 | 8/1997 |
| EP | 686674 B1 | 1/1998 |
| EP | 686675 B1 | 2/1998 |
| EP | 736073 B1 | 3/1998 |
| EP | 690105 B1 | 9/1998 |
| EP | 804512 B1 | 1/1999 |
| EP | 616626 B2 | 11/1999 |
| EP | 741170 B1 | 12/1999 |
| EP | 579091 B2 | 1/2000 |
| EP | 768343 B1 | 2/2001 |
| EP | 763573 B1 | 7/2001 |
| EP | 848044 B1 | 5/2002 |
| EP | 1063959 B1 | 11/2002 |
| EP | 1017755 B1 | 1/2003 |
| EP | 940451 B9 | 2/2003 |
| EP | 1038941 B1 | 5/2003 |
| EP | 948571 B1 | 6/2003 |
| EP | 1165698 B1 | 7/2003 |
| EP | 1230309 B1 | 9/2003 |
| EP | 1078975 B1 | 10/2003 |
| EP | 1009776 B1 | 12/2003 |
| EP | 1078974 B1 | 3/2004 |
| EP | 919599 B1 | 9/2004 |
| EP | 1479730 A1 | 11/2004 |
| EP | 1479731 A1 | 11/2004 |
| EP | 1155097 B1 | 1/2005 |
| EP | 1235882 B1 | 1/2005 |
| EP | 1299079 B1 | 6/2005 |
| EP | 1040821 B2 | 10/2005 |
| EP | 1216277 B1 | 11/2005 |
| EP | 1595921 B1 | 11/2005 |
| EP | 753545 B2 | 5/2006 |
| EP | 1333790 B1 | 8/2006 |
| EP | 1110535 B1 | 2/2007 |
| EP | 1097699 B1 | 5/2007 |
| EP | 1727864 B1 | 7/2007 |
| EP | 1682622 B1 | 8/2007 |
| EP | 1457192 B1 | 2/2008 |
| EP | 1633443 B1 | 3/2008 |
| EP | 1430906 B1 | 6/2008 |
| EP | 1459112 B1 | 10/2009 |
| EP | 1339375 B1 | 11/2009 |
| EP | 2266527 A2 | 12/2010 |
| EP | 2217665 B1 | 6/2011 |
| EP | 1189586 B2 | 10/2011 |
| GB | 1268177 | 7/1978 |
| GB | 1430701 | 9/1978 |
| GB | 1464060 | 11/1978 |
| GB | 1517230 | 3/1981 |
| GB | 1533430 | 1/1998 |
| GB | 2055879 | 5/1998 |
| GB | 1525793 | 7/2005 |
| JP | 10194912 | 3/1972 |
| JP | 10259116 | 4/1976 |

(56) References Cited

FOREIGN PATENT DOCUMENTS

| | | |
|---|---|---|
| JP | 11116438 | 2/1977 |
| JP | 0543417 | 2/1993 |
| JP | 7309715 | 11/1995 |
| JP | 8217638 | 8/1996 |
| JP | 8269357 | 10/1996 |
| JP | 9012430 | 1/1997 |
| JP | 9194754 | 7/1997 |
| JP | 9309819 | 12/1997 |
| JP | 2005187417 | 7/1998 |
| JP | 10017438 | 9/1998 |
| JP | 10114867 | 4/1999 |
| JP | 11116441 | 4/1999 |
| JP | 11124314 | 5/1999 |
| JP | 11222414 | 8/1999 |
| JP | 2000034203 | 2/2000 |
| JP | 2001039847 | 2/2001 |
| JP | 2001288039 | 10/2001 |
| JP | 2002003357 | 1/2002 |
| JP | 2002087935 | 3/2002 |
| JP | 2002241228 | 8/2002 |
| JP | 2003003089 | 1/2003 |
| JP | 2003026537 | 1/2003 |
| JP | 2003171232 | 6/2003 |
| JP | 2003171575 | 6/2003 |
| JP | 2003212723 | 7/2003 |
| JP | 2003213156 | 7/2003 |
| JP | 2003261423 | 9/2003 |
| JP | 2004010541 | 1/2004 |
| JP | 2004123682 | 4/2004 |
| JP | 2004238337 | 8/2004 |
| JP | 2004339185 | 12/2004 |
| JP | 2005126328 | 5/2005 |
| JP | 2005255633 | 9/2005 |
| JP | 2005314390 | 11/2005 |
| JP | 2005314391 | 11/2005 |
| JP | 2005314392 | 11/2005 |
| JP | 2005314394 | 11/2005 |
| JP | 2005314396 | 11/2005 |
| JP | 2005350407 | 12/2005 |
| JP | 2006045562 | 2/2006 |
| JP | 2006328070 | 12/2006 |
| JP | 2007126482 | 5/2007 |
| JP | 2007291066 | 11/2007 |
| JP | 2008230997 | 10/2008 |
| JP | 2008255012 | 10/2008 |
| JP | 2009173606 | 8/2009 |
| JP | 2009185029 | 8/2009 |
| JP | 2009280507 | 12/2009 |
| JP | 2009280542 | 12/2009 |
| JP | 2010083792 | 4/2010 |
| JP | 2010105936 | 5/2010 |
| JP | 2010126445 | 6/2010 |
| JP | 2010235489 | 10/2010 |
| JP | 2010235530 | 10/2010 |
| JP | 2010280607 | 12/2010 |
| WO | WO 9603962 | 2/1996 |
| WO | WO 9634917 | 11/1996 |
| WO | WO 9739066 | 10/1997 |
| WO | WO 9850471 | 11/1998 |
| WO | WO 0051551 | 9/2000 |
| WO | WO 0075240 | 12/2000 |
| WO | WO 0216505 | 2/2002 |
| WO | WO 2004007624 | 1/2004 |
| WO | WO 2004/100922 | 11/2004 |
| WO | WO 2006097352 | 9/2006 |
| WO | WO 2007/031970 | 3/2007 |
| WO | WO 2007055529 | 5/2007 |
| WO | WO 2007093334 | 8/2007 |
| WO | WO 2007118570 | 10/2007 |
| WO | WO 2007140897 | 12/2007 |
| WO | WO 2008007334 | 4/2008 |
| WO | WO 2008074654 | 6/2008 |
| WO | WO 2008092529 | 8/2008 |
| WO | WO 2008132042 | 11/2008 |
| WO | WO 2008135383 | 11/2008 |
| WO | WO 2009071529 | 6/2009 |
| WO | WO 2009135784 | 11/2009 |
| WO | WO 2009152907 | 12/2009 |
| WO | WO 2010050194 | 5/2010 |
| WO | WO 2010057968 | 5/2010 |
| WO | WO 2010063430 | 6/2010 |
| WO | WO 2010146570 | 12/2010 |
| WO | WO 2011079160 | 6/2011 |
| WO | WO 2011085780 | 7/2011 |
| WO | WO 2011095326 | 8/2011 |
| WO | WO 2012046798 | 4/2012 |

PIGMENTED SKIN-CARE COMPOSITIONS

FIELD OF THE INVENTION

The present invention relates to skin care compositions and, in particular, pigmented skin care compositions that are useful in improving the visible appearance of skin.

BACKGROUND OF THE INVENTION

A variety of products are available to consumers to aid in improving skin appearance, and in particular minimizing the visibility of discontinuities in skin appearance. One way to accomplish this is through the use of compositions including colored pigments. For example, cosmetic foundations (either in powdered or lotion form) contain colored pigments that are intended to mimic the skin's natural color. A problem with foundations of this type is that if such foundations are applied in a localized manner (e.g. only in a selected area of redness) the difference between the foundation color and the surrounding natural skin color may be readily apparent resulting in an irregular skin appearance. Alternatively, if such foundations are applied in a continuous manner over a larger area of skin, to thereby provide a more uniform skin appearance, an artificial "mask-like" appearance may result. It is further noted that in order to effectively conceal skin discontinuities, foundations of the type described above require relatively high pigment contents, which further contributes to the undesirable "mask-like" qualities of such compositions.

Certain colored lotions known in the art are specifically intended to reduce "redness", that is reduce the red appearance of certain skin discontinuities. These redness reduction lotions typically rely upon classic pigments or dyes that appear green (the complementary color of red) to thereby deliver the redness reduction effect. The problem with such redness reduction lotions is that they can impart an unnatural green color to the healthy skin surrounding the skin discontinuity.

Efforts have been made to overcome the shortcomings of the products described above by way of personal care compositions that utilize interference pigments, in lieu of conventional pigments. Interference pigments typically are thin plate-like, colorless, particles including two or more layers. The layers of the interference pigment have different refractive indices, and reflect a color resulting from the constructive or destructive interference of reflections of light from the different layers.

A specific skin care composition including interference pigments is disclosed in US Patent Publication 2007065381A to Elsbrock, et al. Elsbrock discloses a skin care composition that includes a first pigment that reflects a first color and a second pigment that reflects a second complementary color.

The inventors of the present invention have discovered that one drawback of the composition disclosed in Elsbrock et al. is that a formulator making a composition in accordance with the teachings of Elsbrock et al. is limited in the selection of interference pigments that may be employed. Specifically, since the composition of Elsbrock et al. requires the use of a combination of a first and second pigment that reflect complementary colors, a formulator is thus limited in the selection of interference pigments that may be employed. In addition, the inventors of the present invention have discovered that if redness reduction is desired, using a composition of the type disclosed in Elsbrock et al., may require the use of relatively high total pigment concentrations. Finally, the inventors of the present invention have discovered that since the composition of Elsbrock et al. requires the use of a combination of a first and a second pigment that are complementary colors, if the chroma of the composition is to be minimized the first and second pigments must be employed in a 1:1 ratio or substantially similar ratio.

In view of the above, the inventors have recognized that further improvements in skin care compositions including interference pigments are required. More specifically, the inventors of the present invention have recognized the need for compositions that minimize the red appearance of certain skin discontinuities with minimal impact on the appearance of the healthy skin surrounding the skin discontinuity. The inventors of present invention have also recognized the need for skin care compositions including interference pigments that can effectively reduce the red appearance of certain skin discontinuities at low total pigment concentrations. Finally, the inventors of the present invention have recognized the need for skin care compositions including at least a first and second interference pigment that have a relatively low chroma over a wide range of first and second pigment ratios.

SUMMARY OF THE INVENTION

In view the of the foregoing, the present invention provides a skin care composition including a dermatologically acceptable carrier, at least a first and a second interference pigment, wherein the composition has a redness reduction index (RRI) of less than −7, and wherein a chroma of the composition is greater than 3.5.

DETAILED DESCRIPTION OF THE INVENTION

All percentages listed in the specification are percentages by weight, unless otherwise specifically mentioned.

As used herein, the term "skin care" means the treatment of the human body, in certain embodiments preferably topical treatment, including, but not limited to application of composition to mammalian skin to improve the appearance of the skin, including the self-perception of one's skin. While the term "skin," is meant broadly, to include all keratinacious parts of the body (including hair and nails), in certain preferred embodiments "skin" is meant to be exclusive of hair and nails.

The present inventors have surprisingly found that it is possible to minimize the visibility of discontinuities in mammalian skin and improve the overall skin appearance by using skin care compositions according to the present invention. Skin care compositions according to the present invention include at least a first and second interference pigment. Skin care compositions according to the present invention may optionally include more than two interference pigments.

Herein, "minimize the appearance of visible discontinuities in mammalian skin" means improving the appearance of mammalian skin such that positive change in skin appearance after topically applying the composition of the present invention to the skin is observed at a distance of two feet from the user, relative to the appearance of the skin prior to application of the composition. "Visible discontinuities" include, but are not limited to, discoloration due to hyper-pigmentation, age spots, freckles, acne, scar tissue, wound, abrasion, under-eye circles, and uneven skin tone.

Applicants have also surprisingly found that it is possible to reduce the red appearance of certain skin discontinuities with minimal impact on the appearance of the healthy skin surrounding said skin discontinuity by using skin care compositions according to the present invention.

The compositions of the present invention include "interference pigments." Interference pigments typically are thin plate-like, colorless, particles including two or more layers. The layers of the interference pigment have different refractive indices, and reflect a color resulting from the constructive or destructive interference of reflections of light from the different layers. Certain interference pigments that are useful in the present invention are those that are formed from mica or borosilicate flakes coated with thin films of $TiO_2$ or $Fe_2O_3$.

Interference pigments suitable for use in compositions of the present invention have a particle size range wherein fifty percent of the particles fall within the size range (D50) of about 2 μm and about 75 μm. Particle size may be determined using a Malvern Mastersizer S particle size analyzer, commercially available from Malvern Instruments Ltd., Worcestershire, United Kingdom. When the term "particle size" is used herein this term is meant to refer to the D50 particle size.

Commercially available interference pigments suitable for use in the present invention are available from BASF Corporation, Florham Park, N.J. (select pigments from those sold under the Flamenco®, Lumina® and Reflecks® tradenames), from Impact Colors, Inc., Newark, Del. (select pigments from those sold under the Gemini™ tradename), and from Kobo Products, Inc., South Plainfield, N.J. (select pigments from those sold under the KTZ™ tradename).

In certain embodiments of the present invention, the composition includes at least a first and second interference pigment wherein the first interference pigment has a hue angle (h°) between 180°-224° and wherein the second interference pigment has a hue angle (h°) between 45°-135°. In certain embodiments of the present invention the second interference pigment has a hue angle (h°) between 80°-95°. Hue angle (h°) was measured using an X-Rite MA98 Multi-Angle Spectrophotometer, commercially available from X-Rite, Inc., Grand Rapids, Mich. To determine the hue angle (h°) of each of the pigments used in the inventive compositions described in detail herein, a 3% pigment in lacquer (clear nail lacquer Sally Hansen, Hard as Nails, Nail Color 4860-01 Invisible, commercially available from Coty, Inc., New York, N.Y.) suspension was formulated. The suspension was drawn down onto the black portion of a Laneta Test Opacity Chart 2A, using an Elcometer 4340 Motorized Applicator machine (the Elcometer 4340 is commercially available from Elcometer Ltd of Manchester, UK; Leneta test charts are commercially available from The Leneta Company, Mahwah, N.J.). The drawdown was performed onto the test card at a speed setting of 1 with the bird applicator, resulting in a 8 mil application in a 3" wide area. After coating the test card, the card was then allowed to dry overnight prior to taking measurements. Measurements were taken of the test card using the 45as15 and 45as45 settings on the X-Rite MA98 Multi-Angle Spectrophotometer to measure the hue angle (h°).

In order for a pigment to be useful in compositions according to the present invention, and therefore considered within the scope of the present invention, the measured hue angle (h°) at both settings must fall within the specified range of between 180°-224° for the first interference pigment or between 45°-135° for the second interference pigment. In certain embodiments of the invention the second interference has a hue angle (h°) between 80°-95°. If the measured hue angle (h°) for a pigment is outside the specified range at either setting (i.e. at 45as15 and 45as45) then the pigment is considered outside the scope of the present invention.

Herein, "chroma," describes color and color intensity. For the purposes of the present invention, color is defined according to a value on the CIELAB color system, which is based on the XYZ color system, defined by the Commission Internationale de l'Eclairage (CIE system) to provide a manner of objectively representing perceived color and color differences. X, Y and Z can be expressed in a variety of manners, or "scales," one of which is the Hunter scale. The Hunter scale has three variables, L, a, and b, which correlate mathematically to X, Y and Z, and is described by Robertson, A. R. in "The nCIE 1976 Color Difference Formulas," *Color Research Applications*, vol. 2, pp. 7-11 (1977). The compositions of the present invention may be analyzed with a Konica Minolta CR-400 Chroma Meter (commercially available from Konica Minolta Sensing Americas, Inc., Ramsey, N.J.), which generates values for L, a, and b. The value for "a" correlates to a value along the red-green (horizontal) axis, and the value for "b" correlates to a value along the blue-yellow (vertical) axis. For example, a blue-colored sample will have a negative b-value, whereas a red-colored sample will have a positive a-value. A more positive or negative value represents a more intense color. The value for "L" is an indicator of lightness and/or darkness, and correlates to a value along the z-axis, which is perpendicular to both the horizontal and vertical axes. "Chroma" is measured by a vector having its origin at the intersection of the red-green and blue-yellow axes and extending outward into the color space defined by the horizontal and vertical axes of the CIELAB color system. The length of the vector represents the chroma, and the direction of the vector represents the shade, or hue. The shorter the vector, the less colored is the composition, and the lower the chroma.

The inventors of the present invention have discovered that skin care compositions of the present invention can be effectively employed to reduce the red appearance of skin discontinuities with minimal impact on the appearance of the surrounding healthy skin. As noted above, skin care compositions according to the present invention include at least a first and second interference pigment. Surprisingly, the inventors of the present invention have discovered that the redness reduction benefit can be delivered by way of the skin care compositions of the present invention over a relatively wide range of first and second interference pigment ratios. In particular, in certain embodiments, skin care compositions of the present invention can deliver the redness reduction benefit over a first interference pigment to second interference pigment ratio range between 20:80 and 80:20.

The inventors of the present invention have discovered that the interference pigments used in the inventive compositions have unique properties when used in combination. Specifically, the interference pigments of certain embodiments of the present invention when used in combination provide a relatively low chroma over a wide range of pigment ratios. In particular, in certain embodiments of the invention, the first and second interference pigments may be employed over the entire 20:80 to 80:20 ratio range and all of such compositions will have a chroma of less than 8.5 when formulated using a substantially colorless carrier of the type described in Table 4 herein. Accordingly, when the language "wherein chroma of said composition over the entire range is less than 8.5" is used herein it means that when a plurality of different compositions are formulated using the first and second interference pigments employed in the inventive composition, and a substantially colorless carrier of the type set for in Table 4, all of such compositions will have a chroma less than 8.5. For example, if a plurality of compositions are formulated using first and second interference pigments according to certain embodiments and the carrier set forth in Table 4 at the pigment ratios of 20:80; 30:70; 40:60; 50:50; 60:40; 70:30; and 80:20 all of such compositions will have a chroma of less than 8.5. The above properties provide the formulator significantly more flexibility than the compositions disclosed in the prior art in that the formulator can provide a relatively low chroma composition over a wide range of first to second pigment ratios.

The inventors of the present invention have discovered that skin care compositions of the present invention can be effectively employed to reduce the red appearance of certain skin discontinuities with minimal impact on the appearance of the surrounding healthy skin. Surprisingly, the inventors of the present invention have discovered that this benefit can be delivered by way skin care compositions according to the present invention having relatively low total pigment concentrations. In particular, the compositions of the present invention may comprise a total amount of interference pigments of from 0.1% to 5% by weight, and in certain embodiments from 1.0% to 4%.

The inventors of the present invention have discovered that skin care compositions of the present invention can be effectively employed to reduce the red appearance of certain skin discontinuities with minimal impact on the appearance of the surrounding healthy skin. Surprisingly, the inventors of the present invention have discovered that this benefit can be delivered despite the skin care compositions not having a chroma that approaches zero. In particular, compositions according to certain embodiments of the present invention have a chroma greater than 3.5, and certain embodiments between 4.0 and 15.0.

Compositions of the present invention include a carrier useful for delivering the pigment to the human body. In certain embodiments the composition includes a cosmetically-acceptable carrier that is useful for distributing the pigment evenly across an expanse of skin. As used herein, the term "cosmetically-acceptable carrier" means a carrier that is suitable for use in contact with the skin without undue toxicity, incompatibility, instability, irritation, allergic response, and the like. This term is not intended to limit the carrier for use solely as a cosmetic (e.g., the ingredient/product can be used as a pharmaceutical).

The cosmetically-acceptable topical carrier generally includes one or more of the following fluids: water, hydrophobic compounds (e.g., hydrocarbons suitable for use in cosmetic products, such as those having carbon chains from about C6 to about C50, more preferably from about C8 to about C22, such as oils, fatty esters, fatty alcohols, fatty esters; as well as silicone fluids/oils) such as ones suitable to provide emolliency, spreadability, or phase stability; glycols such as ones suitable to provide humectancy such as glycerol, or diols such as propylene glycol or butylene glycol; or lower alcohols such as those suitable to provide solvency or spreadability such as ethanol or isopropanol.

In certain embodiments the carrier may include one or more solid, semi-solid, paste-like, or powder materials useful in helping to distribute the pigment across the skin. Examples include hydrophobic compounds, including waxes and other hydrophobic compounds that melt above ambient temperature; powders such as starch, talc, corn starch and the like.

In a preferred embodiment, the embodiment, the cosmetically acceptable topical carrier is present in a concentration that is from about 20% to about 99.9%, preferably form about 50% to about 99.8%, more preferably from about 75% to about 99.5%. In another embodiment, the cosmetically-acceptable topical carrier includes a substrate useful for wiping the composition onto the skin. In yet another embodiment, the cosmetically-acceptable topical carrier includes a bandage for applying the composition to the skin and/or maintaining the composition in contact with the skin.

Preferably the cosmetically acceptable topical carrier is substantially colorless. That is, the carrier does not impart any substantial color to the overall composition independent of the interference pigments employed in the composition. A suitable substantially colorless carrier is disclosed in the Table 4 although other substantially colorless carriers will be readily apparent to those of skill in the art.

The interference pigments may be distributed into the composition via techniques known to those skilled in the art. For example, the pigment may be suspended or dispersed into an oil phase and/or a water phase that is present in the composition. In order to facilitate distribution of the pigment within the composition, the composition may include a stabilizing agent (e.g., a rheology modifier, a thickening agent, a dispersing agent, or similar materials). Any of a variety of commercially available stabilizing agents which are capable of imparting the appropriate viscosity to the compositions are suitable for use in this invention. If used, the thickener may, for example, be present in an amount sufficient to raise the Brookfield viscosity of the composition to a value of between about 500 to about 10,000 centipoise. Examples of suitable thickening agents nonexclusively include: crosslinked polyacrylic acids (e.g., CARBOPOL ULTREZ 10 from Noveon, Inc. of Cleveland, Ohio); mono or diesters of 1) polyethylene glycol of formula: HO—$(CH_2CH_2O)_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; hydrophobically-modified alkali swellable emulsions (HASEs); hydrophobically-modified ethoxylated urethanes (HEURs); xanthan and guar gums; and mixtures thereof.

The composition may include any of various surfactants, wetting agents, or emulsifiers commonly used in personal care formulations. These materials may be ionic, non-ionic, as may be selected for their ability to provide wetting, emulsification, low irritation, foam (or lack thereof), or other desired properties. Examples of suitable surfactants, wetting agents, or emulsifiers include anionics such as surfactants include those selected from the following classes of surfactants: alkyl sulfates, alkyl ether sulfates, alkyl monoglyceryl ether sulfates, alkyl sulfonates, alkylaryl sulfonates, alkyl sulfosuccinates, alkyl ether sulfosuccinates, alkyl sulfosuccinamates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates; nonionic surfactants such as polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester; amphoterics such as amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkyliminodipropionates; alkylamphoglycinates (mono or di); alkylamphopropionates (mono or di),); N-alkyl β-aminoproprionic acids; alkylpolyamino carboxylates; and cationics such as alkyl quaternaries (mono, di, or tri), benzyl quaternaries, ester quaternaries, ethoxylated quaternaries, alkyl amines.

The compositions may include any of various other functional ingredients such as chelating agents (e.g., EDTA); pH adjusters (citric acid, sodium hydroxides, and the like); preservatives; and the like.

Furthermore, compositions of the present invention may also include a skin benefit agent. A skin benefit agent is any element, an ion, a compound (e.g., a synthetic compound or a compound isolated from a natural source) or other chemical moiety in solid (e.g. particulate), liquid, or gaseous state and compound that has a cosmetic or therapeutic effect on the skin. As used herein, the term "benefit agent" includes any active ingredient such as a cosmetic or pharmaceutical, that is to be delivered into and/or onto the skin, hair, mucosa, or teeth at a desired location.

Examples of suitable benefit agents include those that provide benefits such as, but not limited to: de-pigmentation agents; amino acids and their derivatives; antimicrobial agents; allergy inhibitors; anti-acne agents; anti-aging agents including anti-wrinkling agents and benefit agents suitable for treating loss of skin elasticity, uneven skin, blotchiness, and skin tone; tropoelasin promoters and tropoelastin crosslinkers; antiseptics; analgesics; antipruritics; local anesthetics; anti-hair loss agents; hair growth promoting agents; hair growth inhibitor agents, antihistamines; antiinfectives; anti-inflammatory agents; anticholinergics; vasoconstrictors; vasodilators; wound healing promoters; peptides, polypeptides and proteins; deodorants and anti-perspirants; medicament agents; skin firming agents, vitamins; skin lightening agents; skin darkening agents; antifungals; depilating agents; counterirritants; enzymes for exfoliation or other functional benefits; enzyme inhibitors; NFκB-inhibitors; herbal extracts; flavenoids; sensates and stress-reducing agents; anti-oxidants; hair lighteners; sunscreens; anti-edema agents, neo-collagen enhancers, anti-dandruff/sebhorreic dermatitis/psoriasis agents; keratolytics; and mixtures thereof.

Particularly suitable benefit agents include depigmentation agents and skin-lightening agents such as hydroquinone and extracts of soy; keratolytic agents and/or anti-acne agents such as alpha and beta hydroxyacids such as salicylic acid; anti-aging actives such as retinoids including retinol, amines such as N,N,N',N'-Tetrakis(2-hydroxypropyl)ethylenediamine (THPED), N,N,N',N'-Tetrakis(2-hydroxyethyl) ethylene diamine (THEED), N,N,N',N'-tetramethylethylene diamine (TEMED), substituted resorcinols such as 4-hexyl resorcinol, anti-inflammatories such as extracts of feverfew, tropoelastin promoters such as extracts of blackberry, tropoelastin crosslinkers such as extracts of dill, among other skin benefit agents.

The amount of the benefit agent that may be used may vary depending upon, for example, the ability of the benefit agent to penetrate through the skin, nail, mucosa, or teeth; the specific benefit agent chosen, the particular benefit desired, the sensitivity of the user to the benefit agent, the health condition, age, and skin and/or nail condition of the user, and the like. In sum, the benefit agent is used in a "safe and effective amount," which is an amount that is high enough to deliver a desired skin or nail benefit or to modify a certain condition to be treated, but is low enough to avoid serious side effects, at a reasonable risk to benefit ratio within the scope of sound medical judgment.

The compositions may be made into a wide variety of product types that include but are not limited to cleansing liquid washes, gels, sticks, sprays, solid bars, shampoos, pastes, foams, powders, mousses, wipes, patches, hydrogels, and films. These product types may comprise several types of cosmetically-acceptable carriers including, but not limited to solutions, emulsions (including for example, oil-in-water, water-in-oil, microemulsions and nanoemulsions, and the like), gels, and solids. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically acceptable aqueous or organic solvent). Examples of suitable organic solvents include: polyglycerols, propylene glycol, polyethylene glycol (200, 600), polypropylene glycol (425, 2025), glycerol, 1,2,4-butanetriol, sorbitol esters, 1,2,6-hexanetriol, ethanol, and mixtures thereof. In certain preferred embodiments, the compositions of the present invention are aqueous solutions comprising from about 50% to about 99% by weight of water.

According to certain embodiments, compositions useful in the subject invention may be formulated as a solution comprising an emollient. Such compositions preferably contain from about 2% to about 50% of an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32 43 (1972) and the International Cosmetic Ingredient Dictionary and Handbook, eds. Wenninger and McEwen, pp. 1656 61, 1626, and 1654 55 (The Cosmetic, Toiletry, and Fragrance Assoc., Washington, D.C., 7.sup.th Edition, 1997) (hereinafter "ICI Handbook") contains numerous examples of suitable materials. A lotion can be made from such a solution. Lotions typically comprise from about 1% to about 20% (e.g., from about 5% to about 10%) of an emollient(s) and from about 50% to about 90% (e.g., from about 60% to about 80%) of water.

The present compositions may be of varying phase compositions, including those having an exterior aqueous phase (e.g., aqueous phase is the most exterior phase of the composition). As such, compositions of the present invention may be formulated to be oil-in-water emulsions that are shelf-stable in that the emulsion does not lose phase stability or "break" when kept at standard conditions (22 degrees Celsius, 50% relative humidity) for a week or more after it is made.

For those compositions that include an aqueous phase, the pH of the present compositions is not critical, but may be in a range that does not facilitate irritation to the skin, such as from about 4 to about 7. The viscosity of the personal care composition is not critical, although it may be a spreadable cream or lotion or gel.

The pigment, carrier and optional other components of the composition may be combined according to the present invention via any conventional methods of combining two or more fluids or solids. For example, one or more compositions comprising, consisting essentially of, or consisting of at least one pigment and one or more compositions comprising, consisting essentially of, or consisting of water or suitable ingredients may be combined by pouring, mixing, adding dropwise, pipetting, pumping, and the like, one of the compositions comprising the polymerized surfactant into or with the other in any order using any conventional equipment such as a mechanically stirred propeller, paddle, and the like.

In certain embodiments, the composition may be impregnated within a substrate (e.g., non-woven fibrous material, a film material, or combinations thereof). The substrate material may be selected to facilitate depositing the pigment on the skin.

The methods of the present invention may further comprise any of a variety of steps for mixing or introducing one or more of the optional components described hereinabove with or into a composition comprising the pigment, either before, after, or simultaneously with the combining step described above.

In certain embodiments, the compositions produced via the present invention are preferably used as or in personal care products for treating at least a portion of a mammalian body, for example, the human body. Examples of certain preferred personal care products include various products suitable for application to the skin or hair. Particularly preferred products are those that are designed to be applied to the skin and not immediately rinsed off. Examples of these "leave-on" products particularly for use on the face, but also including those for the body, hands, feet, and the like.

As discussed above, the inventors of the present invention have surprisingly found that it is possible to reduce the red appearance of skin discontinuities with minimal impact on the appearance of the healthy skin surrounding said skin discontinuity by using skin care compositions according to the present invention. The Redness Reduction Index (RRI) Test set forth in detail below was used to illustrate the inventive skin care compositions ability to reduce the red appearance of skin discontinuities. The Healthy Skin Color Change Value (HSCCV) Test set forth in detail below was used to illustrate inventive skin care compositions ability to deliver redness reduction with minimal impact on the appearance of the healthy skin surrounding the skin discontinuity. The inventors of the present invention have further discovered that in order for a skin care composition to preserve the natural tone of healthy skin it cannot impart a "green" tone to the healthy skin. Furthermore, any such green tone must not be visible when the skin is viewed from multiple angles since the human eye simultaneously views a surface from multiple angles. The Multi-Angle Δa* (MADA) Test set forth below was used to illustrate the inventive skin care compositions ability to preserve the natural tone of healthy skin without imparting a "green" tone thereto when the skin is viewed from multiple angles.

Redness Reduction Index (RRI) Test

A test card including a first portion that is representative of a healthy Caucasian skin color and a second portion that is representative of an inflamed skin discontinuity was prepared as follows. The test card had dimensions of 4"×6" and was formed from Olympus P100 photo paper. The photo paper was printed using an Olympus P-10 printer which was loaded with the bundled ink ribbon. The first and second portions, each measuring 1.3"×6", were created by entering the RGB values, set forth in Table 1 below, into MATLAB R2011a software (commercially available from Mathworks, Inc., Natick, Mass.) and then printing the test card.

TABLE 1

|  | R | G | B |
|---|---|---|---|
| Healthy Skin | 238 | 203 | 181 |
| Inflamed Skin | 170 | 53 | 65 |

A mimic stratum corneum overlay was prepared as follows. A stratum corneum mimic layer formed from VITRO-CORNEUM® (commercially available from IMS, Inc., Portland, Me.) was attached in a non-hydrated state to a cellulose acetate slide measuring 5"×7" (PP2500 Transparency Film for Plain Paper Copiers, commercially available from 3M, St. Paul, Minn.) using collagen glue (Resine ou Pigment Pur, concentration 8% in water, commercially available from Sennlier, Paris, France) such that it covered the entire slide, with the rough surface of the VITRO-CORNEUM® facing outward. After setting, the prepared substrate was cut into strips measuring 1.5 cm×6.0 cm, each strip constituting one mimic stratum corneum overlay.

After printing of the test card, the color of the test card was assessed using a Hunter UltraMax Colorimeter (commercially available from Hunter Associates Laboratory, Inc., Reston, Va.), both with and without the mimic stratum corneum overlay. The readings for the test card alone are set forth in Table 2 below and the readings for the test card measured through the mimic stratum corneum overlay (i.e. with the stratum corneum overlay on top of the test card, with the VITRO-CORNEUM® surface facing towards the measurement device) are set forth in Table 3 below.

TABLE 2

| | Test Card | | |
|---|---|---|---|
| | L* | a* | b* |
| Healthy Skin | 84.28 | 9.71 | 16.05 |
| Inflamed Skin | 40.71 | 48.60 | 21.08 |

TABLE 3

| | Test Card with Mimic Stratum Corneum Overlay | | |
|---|---|---|---|
| | L* | a* | b* |
| Healthy Skin | 81.45 | 9.21 | 16.54 |
| Inflamed Skin | 48.86 | 22.22 | 10.61 |

The pigmented skin care composition to be assessed was finger applied on the mimic stratum corneum overlay in an amount of 2.5 mg/cm$^2$ and smoothed until a consistent layer was attained and then allowed to dry at room temperature overnight. To assess the pigmented skin care composition's impact on the inflamed and healthy skin color targets, the treated mimic stratum corneum overlay was placed over the two color targets on the test card and using a Hunter UltraMax colorimeter, L*, a* and b* values were measured over both portions of the test card, that is separate L*, a* and b* measurements were conducted over the "Healthy Skin" portion of the test card through the treated mimic stratum corneum overlay and separately over the "Inflamed Skin" portion of the test card through the treated mimic stratum corneum overlay.

Using the measured values for a* over the "Inflamed Skin" portion, and the original a* value of the test card over the "Inflamed Skin" portion of the test card set forth in Table 3 above, Δa* was calculated according to the equation $\Delta a^* = a^*_2 - a^*_1$, where $a^*_2$ is the a* value measured through the treated mimic stratum corneum overlay over the "Inflamed Skin" portion of the test card and $a^*_1$ is the original a* value set forth in Table 3 above for the "Inflamed Skin" portion of the test card measured through the non-treated mimic stratum corneum overlay. This measured value of Δa* indicates the ability of the test composition to reduce the "red" appearance of a skin discontinuity, the more "negative" the Δa* value the greater the redness reduction capabilities of the test composition.

The above described test was repeated four (n=4) times for each test composition. An average was taken of each of the four calculated Δa* values to provide an average Δa* value. This average Δa* is referred to herein as the Redness Reduction Index (RRI).

Compositions according to the present invention have a redness reduction index (RRI) of less than −7, in some embodiments less than −7.5, in some embodiments less than −9.5, in some embodiments between −7.5 and −16.0, and in some embodiments between −10.0 and −16.0.

Healthy Skin Color Change Value (HSCCV) Test

Using the values for L*, a* and b* measured through the treated mimic stratum corneum overlay over the "Healthy Skin" portion of the test card, and the original L*, a* and b* values of the "Healthy Skin" of the test card measured through the non-treated mimic over the "Healthy Skin" portion of the test card (set forth in Table 3 above), the ΔE of the "Healthy Skin" portion of the test card was determined according to the formula set forth below.

$$\Delta E = \sqrt{((L^*_2 - L^*_1)^2 + (a^*_2 - a^*_1)^2 + (b^*_2 + b^*_1))}; \text{ where}$$

$L^*_2$, $a^*_2$, and $b^*_2$=L*, a* and b* value of test card in the healthy skin portion of the card as measured through the treated mimic stratum corneum layer; and $L^*_1$, $a^*_1$ and $b^*_1$=L*, a* and b* value of test card in the healthy skin portion of the card as measured through the non-treated mimic stratum corneum layer (set forth in Table 3 above).

The calculated ΔE value indicates the degree to which the test composition changed the appearance of healthy skin, the smaller the ΔE value the less the test composition altered the appearance of healthy skin.

The above described test was repeated four (n=4) times for each test composition. An average was taken of each of the four calculated ΔE values to provide an average ΔE value. This average ΔE is referred to herein as the Healthy Skin Color Change Value (HSCCV). Compositions according to the present invention have an HSCCV of less than 3 and in certain embodiments between 0 and 2.5. In this regard, it is noted that the human eye can barely detect a ΔE≈2.3. (Gaurav Sharma (2003). *Digital Color Imaging Handbook* (1.7.2 ed.). *CRC Press. ISBN 0-8493-0900-X*)

Compositions of the present invention simultaneously provide a negative RRI and a small HSCCV. The combination of a negative RRI and a small HSCCV indicates that the inventive compositions are both effective at reducing the red appearance of skin discontinuities while at the same time have minimal impact on the appearance of the surrounding healthy skin.

Chroma Measurement Test

For each of the test compositions tested above, the chroma of such composition was determined as follows.

Three grams (3 g) of the test composition was drawn down onto an AF4300 Write-On Transparency Film (commercially available from 3M, St. Paul, Minn.). The drawdown was conducted by hand using the 6 mil side of a 2-path, 5 inch applicator, part #663479, Precision Gage and Tools Co., Dayton, Ohio After coating the transparency was allowed to dry overnight prior to taking measurements. After drying, the transparency was placed over the black portion of Laneta Test Opacity Chart 2A (commercially available from The Leneta Company, Mahwah, N.J.).

Using a Konica Minolta CR-400 Chroma Meter (commercially available from Konica Minolta Sensing Americas, Inc., Ramsey, N.J.), L*, a* and b* values were measured over the black portion of the test card. Using these values, chroma for the test composition was calculated according to the following equation.

$$\text{Chroma} = \sqrt{(a^{*2} + b^{*2})}$$

The above described test was repeated three (n=3) times for each test composition. An average Chroma value was taken from the four calculated Chroma values to provide an average Chroma value. Compositions according to certain embodiments of the present invention have an average chroma greater than 3.5, and in certain embodiments between 4.0 and 15.0.

Multi-Angle Δa*Test (MADA)

For each of the test compositions tested above, the MADA of such composition was determined as follows. Using the same test card and mimic stratum corneum overlay described above in the Redness Reduction Index (RRI) Test, an a* reading was measured for the Healthy Skin portion of the test card through the mimic stratum corneum overlay using an X-Rite MA98 Multi-Angle Spectrophotometer, commercially available from X-Rite, Inc., Grand Rapids, Mich. It is noted that for purposes of the MADA test the mimic stratum corneum was cut to have dimensions of 3.81 cm×3.81 cm. The a* reading was measured at eight different angles and each of these values was averaged to provide an average a* reading for the Healthy Skin portion of the test card through the mimic stratum corneum overlay. The eight different angles comprised the following angle settings on the test apparatus 45as-15, 45as15, 45as25, 45as45, 45as75, 45as110, 15as-15, and 15as15.

The pigmented skin care composition to be assessed was finger applied on the mimic stratum corneum overlay in an amount of 2.5 mg/cm² and smoothed until a consistent layer was attained and then allowed to dry at room temperature overnight.

An a* reading was measured for the Healthy Skin portion of the test card through the test composition. The a* reading was measured at eight different angles and each of these values was averaged to provide an average a* reading for the Healthy Skin portion of the test card measured through test composition. The eight different angles comprised the following angle settings on the test apparatus 45as-15, 45as15, 45as25, 45as45, 45as75, 45as110, 15as-15, and 15as15.

Using the measured a* values an average Δa* value, or MADA value, was calculated according to the following formula:

$$\Delta a^* = a^*_2 - a^*_1; \text{ where}$$

$a^*_2$=average a* value for the Healthy Skin portion of the test card measured through test composition applied to mimic stratum corneum overlay; and $a^*_1$=average a* value for the Healthy Skin portion of the test card measured through the non-treated mimic stratum corneum overlay.

The above described test was repeated four (n=4) times for each test composition. An average MADA value was taken from the four calculated MADA values to provide an average MADA value. Compositions according to the present invention have an average MADA value of greater than −4.0, and in certain embodiments between −3.5 and 0.3.

INVENTIVE EXAMPLES

Pigmented skin care compositions according to the present invention were formulated to include an oil in water cream carrier and the selected interference pigments. The amount of water in the formulation was adjusted according to the amount of pigment employed in the specific inventive example. The base oil in water cream carrier was selected due to its low optical impact to the L*a*b* measurements conducted according to the test methods set forth above herein. The inventive formulations are summarized in Table 4 below. The pigments employed in each inventive formulation are summarized in Table 5 below. The hue angle (h°) as measured at 45as15 and 45as45 is specified for each pigment used in each of the inventive compositions.

TABLE 4

| Source of Supply | Trade Name | INCI Name | % wt/wt |
|---|---|---|---|
| Water phase | | | |
| N/A | PURIFIED WATER | WATER | 79.95-83.45 |
| Emery Oleochemicals | Emery 917 | Glycerin | 5.00 |
| INIVAR | Carbomer Ultrez 10 | | 0.60 |
| General Chemical Performance Products | 20% SODIUM HYDROXIDE solution | SODIUM HYDROXIDE | Trace (to achieve pH target) |
| Oil phase | | | |
| Dow | VERSENE NA | Disodium EDTA | 0.20 |
| Croda | Brij 72 | Steareth-2 | 0.75 |
| Croda | Brij 721 | Steareth-21 | 1.50 |
| Innospec | Finsolv TN | C12-15 Alkyl Benzoate | 2.00 |
| Dow Corning | DC Q7-9120 Silicone Fluid, 20 cst | Dimethicone | 5.00 |
| Clariant | Phenonip XB | Phenoxyethanol and methyl and ethyl and propyl parabens | 1.00 |
| Pigments | | | |
| Set forth in Table 5 Below | | | 0.50-4.00 |
| Pigment Composition | | | 100.00 |

TABLE 5

| | Pigment Composition |
|---|---|
| Inventive Example #1 | Flamenco Summit Turquoise, 0.4% + Flamenco Summit Gold, 1.6% (45as15-189°, 45as45-193°), (45as15-88°, 45as45-84°) |
| Inventive Example #2 | Flamenco Summit Turquoise, 0.8% + Flamenco Summit Gold, 1.2% (45as15-189°, 45as45-193°), (45as15-88°, 45as45-84°) |
| Inventive Example #3 | Flamenco Summit Turquoise, 1.2% + Flamenco Summit Gold, 0.8% (45as15-189°, 45as45-193°), (45as15-88°, 45as45-84°) |
| Inventive Example #4 | Flamenco Summit Turquoise, 1.6% + Flamenco Summit Gold, 0.4% (45as15-189°, 45as45-193°), (45as15-88°, 45as45-84°) |
| Inventive Example #5 | Flamenco Summit Turquoise, 1% + Flamenco Summit Gold, 3% (45as15-189°, 45as45-193°), (45as15-88°, 45as45-84°) |
| Inventive Example #6 | Flamenco Summit Turquoise, 1% + Flamenco Summit Gold, 2% (45as15-189°, 45as45-193°), (45as15-88°, 45as45-84°) |
| Inventive Example #7 | Flamenco Summit Turquoise, 1% + Flamenco Summit Gold, 1% (45as15-189°, 45as45-193°), (45as15-88°, 45as45-84°) |
| Inventive Example #8 | Flamenco Summit Turquoise, 1.32% + Flamenco Summit Gold, 0.66% (45as15-189°, 45as45-193°), (45as15-88°, 45as45-84°) |
| Inventive Example #9 | Flamenco Summit Turquoise, 0.5% + Flamenco Summit Gold, 0.5% (45as15-189°, 45as45-193°), (45as15-88°, 45as45-84°) |
| Inventive Example #10 | Flamenco Summit Turquoise, 1% + KTZ Interfine Gold, 1% (45as15-189°, 45as45-193°), (45as15-91°, 45as45-84°) |
| Inventive Example #11 | Flamenco Summit Turquoise, 1% + KTZ Interfine Gold, 2% (45as15-189°, 45as45-193°), (45as15-91°, 45as45-84°) |
| Inventive Example #12 | Flamenco Summit Turquoise, 1% + Timiron Splendid Gold, 1% (45as15-189°, 45as45-193°), (45as15-91, 45as45-88°) |
| Inventive Example #13 | Flamenco Summit Turquoise, 1% + Timiron Splendid Gold, 2% (45as15-189°, 45as45-193°), (45as15-91, 45as45-88°) |
| Inventive Example #14 | Lumina Turquoise 9T30D, 1% + Flamenco Summit Gold, 1% (45as15-193°, 45as45-207°), (45as15-88°, 45as45-84°) |
| Inventive Example #15 | Lumina Turquoise 9T30D, 1% + Flamenco Summit Gold, 2% (45as15-193°, 45as45-207°), (45as15-88°, 45as45-84°) |
| Inventive Example #16 | Reflecks MultiDimensions Transforming Teal, 1% + Flamenco Summit Gold, 1% (45as15-193°, 45as45-207°), (45as15-88°, 45as45-84°) |
| Inventive Example #17 | Gemini GB-38, 1% + Flamenco Summit Gold, 1% (45as15-210°, 45as45-198°), (45as15-88°, 45as45-84°) |
| Inventive Example #18 | Gemini GB-38, 1% + Flamenco Summit Gold, 2% (45as15-210°, 45as45-198°), (45as15-88°, 45as45-84°) |

In a clean beaker, combine all oil phase ingredients then began agitation and heat to 55-60° C. until the oil phase is homogeneous. In a separate clean beaker, combine water and other water phase ingredients and began agitation and heat to 55-60° C. until the water phase is homogeneous. Add the oil phase to water phase with increased agitation, mixing at a high speed for 8 minutes at 55-60° C. Cool the mixture to 50° C. and then add the Dimethicone. At 40° C., add the Phenonip, and continue mixing until uniform. Continue cooling until a temperature of 30° C. is reached, check the pH and adjust with Sodium Hydroxide solution to a target pH of 5.4 or in a range from 5.2 to 5.7

Disperse the pigment in thirty percent of the deionized water to be contained in the final composition to suspend the particles and mix thoroughly with propeller blade (or spatula depending on batch size) inside a beaker. Combine pigment premix with oil in water cream carrier prepared above in main beaker and mix thoroughly until uniform.

COMPARATIVE EXAMPLES

A total of eight commercial skin care products were evaluated using the test methods described above. The eight commercial products evaluated are listed below.

Comparative Example #1

Eucerin Redness Relief Daily Perfecting Lotion

Comparative Example #2

Dermalogica Sheer Tint Redness Relief

Comparative Example #3

Clearasil ULTRA Overnight Face Lotion

Comparative Example #4

Eucerin Redness Relief Soothing Anti-Aging Serum

Comparative Example #5

Neutrogena Oil Free Acne Stress Control

Comparative Example #6

Clinique Redness Solutions Daily Relief Cream

Comparative Example #7

Estee Lauder Idealist Even Skintone Illuminator

Comparative Example #8

Clinique Redness Solutions Urgent Relief Cream

Additional comparative examples were formulated using the oil in water carrier described above in Table 4 in combination with the pigments set forth below in Table 6.

TABLE 6

| | | |
|---|---|---|
| Comparative Example 9 | KTZ Interfine ™ Blue | 2.5% |
| | KTZ Interfine ™ Gold | 2.5% |
| Comparative Example 10 | KTZ Interfine ™ Red | 1.0% |
| | KTZ Interfine ™ Green | 1.0% |
| Comparative Example 11 | KTZ Interfine ™ Gold | 0.3% |
| | KTZ Interfine ™ Violet | 0.3% |
| Comparative Example 12 | KTZ Interfine ™ Green | 0.83% |
| | KTZ Interfine ™ Violet | 0.34% |
| | Prestige Silk ™ Orange | 0.83% |
| Comparative Example 13 | KTZ Interfine ™ Blue | 0.5% |
| | KTZ Interfine ™ Gold | 0.5% |
| | KTZ Interfine ™ Red | 0.5% |
| | KTZ Interfine ™ Green | 0.5% |
| Comparative Example 14 | Timiron Splendid ™ Gold | 1.0% |
| | Timiron Splendid ™ Blue | 1.2% |
| Comparative Example 15 | Timiron Splendid ™ Gold | 0.4% |
| | Timiron Splendid ™ Blue | 0.35% |
| | KTZ Interval ™ Red | 0.4% |
| | KTZ Interval ™ Green | 0.35% |
| Comparative Example 16 | Prestige Silk ™ Blue | 1.5% |
| | Prestige Silk ™ Gold | 1.5% |
| Comparative Example 17 | KTZ Interval ™ Red | 0.9% |
| | KTZ Interval ™ Green | 0.8% |
| Comparative Example 18 | KTZ Interval ™ Gold-11S2 | 0.75% |
| | KTZ Interval ™ Blue-11S2 | 0.75% |
| Comparative Example 19 | KTZ Interval ™ Gold-11S2 | 0.3% |
| | KTZ Interval ™ Blue-11S2 | 0.3% |
| | KTZ Interval ™ Red-11S2 | 0.3% |
| | KTZ Interval ™ Green-11S2 | 0.3% |
| Comparative Example 20 | Timiron Super Green | 4% |
| Comparative Example 21 11850-164-1 | Timiron Super Green | 3% |

The Inventive Examples and Comparative Examples described above were tested according to the Redness Reduction Index (RRI) Test, Healthy Skin Color Change Value (HSCCV) Test, Chroma Measurement Test and the Multi-Angle Δa* (MADA) Test set forth herein. The results of such test are summarized in the Table of Results set forth below.

TABLE OF RESULTS

| SAMPLE | RRI | HSCCV | Chroma | MADA |
|---|---|---|---|---|
| Inventive Example 1 | −12.3 | 2.4 | 7.3 | −1.1 |
| Inventive Example 2 | −13.2 | 2.3 | 6.1 | −1.5 |
| Inventive Example 3 | −10.9 | 1.8 | 4.8 | −2.8 |
| Inventive Example 4 | −9.9 | 1.6 | 5.5 | −3.8 |
| Inventive Example 5 | −17.3 | 3.6 | 14.3 | −2.4 |
| Inventive Example 6 | −13.6 | 2.4 | 8.1 | −1.7 |
| Inventive Example 7 | −10.8 | 1.7 | 4.9 | −1.1 |
| Inventive Example 8 | −9.9 | 1.4 | 5.3 | −3.5 |
| Inventive Example 9 | −7.2 | 1.0 | 3.7 | −2.0 |
| Inventive Example 10 | −6.3 | 1.3 | 7.1 | −2.1 |
| Inventive Example 11 | −7.7 | 1.5 | 12.3 | −1.7 |
| Inventive Example 12 | −9.0 | 1.4 | 5.4 | −1.2 |
| Inventive Example 13 | −12.4 | 2.1 | 6.1 | −2.7 |
| Inventive Example 14 | −9.0 | 1.4 | 4.1 | −3.4 |
| Inventive Example 15 | −15.4 | 2.7 | 8.1 | −3.1 |
| Inventive Example 16 | −9.7 | 1.3 | 3.6 | 0.2 |
| Inventive Example 17 | −8.6 | 1.5 | 5.5 | −1.5 |
| Inventive Example 18 | −12.9 | 2.4 | 8.1 | −1.0 |
| Comparative Example 1 | −24.1 | 7.0 | 7.3 | −6.9 |
| Comparative Example 2 | −7.6 | 3.2 | 7.6 | −2.3 |
| Comparative Example 3 | 0.0 | 0.6 | 0.2 | 0.8 |
| Comparative Example 4 | −1.3 | 2.1 | 1.1 | −0.1 |
| Comparative Example 5 | −0.9 | 1.2 | 0.8 | 0.8 |
| Comparative Example 6 | −1.8 | 0.5 | 1.2 | 0.8 |
| Comparative Example 7 | −6.8 | 0.6 | 4.5 | 0.7 |
| Comparative Example 8 | −0.8 | 0.4 | 0.8 | 0.6 |
| Comparative Example 9 | −14.1 | 3.5 | 2.1 | −0.9 |
| Comparative Example 10 | −6.9 | 0.9 | 1.3 | 0.1 |
| Comparative Example 11 | −0.9 | 0.4 | 1.3 | 1.5 |
| Comparative Example 12 | −6.8 | 0.9 | 1.0 | 0.3 |
| Comparative Example 13 | −6.0 | 0.9 | 1.2 | 0.2 |

TABLE OF RESULTS-continued

| SAMPLE | RRI | HSCCV | Chroma | MADA |
|---|---|---|---|---|
| Comparative Example 14 | −5.6 | 1.1 | 3.3 | 0.4 |
| Comparative Example 15 | −5.1 | 0.6 | 0.9 | 0.4 |
| Comparative Example 16 | −9.2 | 2.4 | 3.5 | −0.1 |
| Comparative Example 17 | −5.0 | 0.7 | 0.8 | 0.5 |
| Comparative Example 18 | −5.0 | 0.6 | 1.3 | 0.5 |
| Comparative Example 19 | −4.9 | 0.8 | 1.1 | 0.7 |
| Comparative Example 20 | −20.8 | 3.5 | 10.4 | −5.1 |
| Comparative Example 21 | −15.4 | 2.0 | 8.7 | −4.4 |

While particular embodiments of the present have been illustrated and described, it would be obvious to those skilled in the art that various other changes and modifications can be made without department from the spirit and scope of the invention. It is therefore intended to cover in the appended claims all such changes and modifications that are within the scope of this invention.

We claim:

1. A skin care composition comprising:
a dermatologically acceptable carrier;
at least a first and a second interference pigment, wherein the total amount of interference pigments is from 1% to 4% by weight;
wherein the chroma of the composition is greater than or equal to 3.7; and wherein the composition has a healthy skin color change value (HSCCV) of less than or equal to 2.4; and wherein the first interference pigment has a hue angle (h°) between 185°-215° and the second interference pigment has a hue angle (h°) between 80°-95°.

2. The skin care composition according to claim 1, wherein the composition has a redness reduction index (RRI) between −7.5 and −16.0.

3. The skin care composition according to claim 2, wherein the chroma of the composition is between 4.0 and 15.0.

4. The skin care composition according to claim 1, wherein the composition has a redness reduction index (RRI) of less than −7.5.

5. The skin care composition according to claim 1, wherein the composition has a redness reduction index (RRI) of less than −9.5.

6. The skin care composition according to claim 1, wherein the composition has a HSCCV of between 0.5 and 2.4.

7. The skin care composition according to claim 6, wherein the ratio of the percentage of the first interference pigment to the second interference pigment is in the range between 20:80 and 80:20.

8. The skin care composition according to claim 1, wherein the skin care composition additionally comprises at least one skin care active.

9. The skin care composition according to claim 8, wherein the skin care active is selected from the group consisting of depigmentation agents and skin-lightening agents; keratolytic agents; anti-acne agents; anti-aging actives and anti-inflammatories.

10. The skin care composition according to claim 7, wherein each of the first and second interference pigment has a particle size range wherein the range is 2 µm to 75 µm.

11. The skin care composition according to claim 10, wherein the composition has a multi-angle Δa*(MADA) value of greater than −4.0.

12. The skin care composition according to claim 11, wherein the composition has a MADA value of between −3.5 and 0.3.

* * * * *